United States Patent [19]
De Carvalao Castro et al.

[11] Patent Number: 6,127,317
[45] Date of Patent: Oct. 3, 2000

[54] CONCENTRATED, AQUEOUS HERBICIDAL COMPOSITIONS CONTAINING AN IMIDAZOLINYL ACID SALT AND A GLYPHOSATE SALT

[75] Inventors: Kelly Neoob De Carvalao Castro, Copacabana-Rio de Janeiro; Wilson Mendonca, Meier-Rio de Janeiro, both of Brazil

[73] Assignee: American Cyanamid Company, Madison, N.J.

[21] Appl. No.: 09/152,709

[22] Filed: Sep. 14, 1998

Related U.S. Application Data

[60] Provisional application No. 60/059,313, Sep. 17, 1997.

[51] Int. Cl.[7] .............................. A01N 43/50; A01N 57/02
[52] U.S. Cl. ................................................. 504/128
[58] Field of Search ............................................. 504/128

[56] References Cited

U.S. PATENT DOCUMENTS

| | | | |
|---|---|---|---|
| 4,816,060 | 3/1989 | Steller et al. ................................ | 71/92 |
| 5,206,021 | 4/1993 | Dookhith et al. ........................ | 424/405 |
| 5,268,352 | 12/1993 | Dexter ..................................... | 504/206 |
| 5,478,795 | 12/1995 | Watkins, Jr. ............................. | 504/130 |
| 5,597,778 | 1/1997 | Smale ...................................... | 504/127 |
| 5,672,617 | 9/1997 | Wachtler et al. ........................ | 514/407 |

FOREIGN PATENT DOCUMENTS

| | | | |
|---|---|---|---|
| 0220902 | 10/1986 | European Pat. Off. . | |
| 256 414 A2 | 2/1988 | European Pat. Off. ....... | A01N 25/22 |
| 433 577 A1 | 6/1991 | European Pat. Off. ....... | A01N 25/04 |
| 2233229 | 1/1991 | United Kingdom ........... | A01N 57/20 |
| WO 96/08148 | 3/1996 | WIPO ............................. | A01N 41/10 |

OTHER PUBLICATIONS

Bruff et al., "Tank–mix combinations for weed control in stale seedbed soybean (*Glycine max*)", Weed Technology, 6 (1), pp. 45–51 (1992).

Lanie et al., "Herbicide Combinations for Soybean (*Glycine max*) Planted in Stale Seedbed", Weed Technology, 8 (1), pp. 17–22 (1994).

CA124: 281878 abstract of Sanders et al., "Control of nut grass (*Cyperus rotundus*) in asparagus", Proc. N. Z. Plant Prot. Conf., 48th, pp. 322–326 (1995).

*Primary Examiner*—S. Mark Clardy
*Attorney, Agent, or Firm*—John W. Hogan, Jr.

[57] ABSTRACT

The present invention provides concentrated aqueous herbicidal compositions of imidazolinyl acid salts and glyphosate salts.

23 Claims, No Drawings

CONCENTRATED, AQUEOUS HERBICIDAL COMPOSITIONS CONTAINING AN IMIDAZOLINYL ACID SALT AND A GLYPHOSATE SALT

This application claims benefit of Provisional Appl. 60/059,313, filed Sep. 17, 1997.

BACKGROUND OF THE INVENTION

Aqueous compositions containing imidazolinyl acid salts are described in U.S. Pat. No. 4,816,060, and aqueous compositions containing glyphosate salts are described in EP 220,902-A2. However, concentrated, aqueous compositions comprising an imidazolinyl acid salt and a glyphosate salt have not been described. The principal reason that aqueous compositions containing both of those compounds have not been disclosed is that imidazolinyl acid salts and glyphosate salts are, in general, not mutually compatible. Aqueous glyphosate salt compositions generally have a pH value of about 4. However, imidazolinyl acid salts are not entirely stable in an environment having a pH value of about 4. Conversely, glyphosate salts are not entirely stable at the pH values required to provide stable aqueous compositions of imidazolinyl acid salts.

To overcome the incompatibility problems associated with aqueous compositions containing imidazolinyl acid salts and glyphosate salts, emulsifiable suspension concentrate compositions containing imidazolinyl acids and glyphosate have been described (see, e.g., U.S. Pat. No. 5,268,352). However, emulsifiable suspension concentrate compositions are not entirely satisfactory because they require the use of heavy aromatic solvents.

What is needed in the art is an aqueous composition which overcomes the incompatibility problems associated with imidazolinyl acid salts and glyphosate salts without requiring the use of heavy aromatic solvents.

It is, therefore, an object of the present invention to provide a concentrated, aqueous herbicidal composition which contains an imidazolinyl acid salt and a glyphosate salt.

It is also an object of the present invention to provide a process for the preparation of a concentrated, aqueous herbicidal composition which contains an imidazolinyl acid salt and a glyphosate salt.

Those and other objects of the present invention will become more apparent from the detailed description thereof set forth below.

SUMMARY OF THE INVENTION

The present invention relates to a concentrated, aqueous herbicidal composition which comprises about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an anti-foaming agent, up to about 3% w/v of a base, and water, provided that the composition has an initial pH of from about 6.0 to about 7.0.

The present invention also relates to a process for the preparation of the concentrated, aqueous herbicidal compositions of this invention.

DETAILED DESCRIPTION OF THE INVENTION

The storage stable herbicidal compositions of this invention comprise about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 3% w/v of a base, and water, provided that the composition has an initial pH of from about 6.0 to about 7.0.

In a preferred embodiment of the present invention, the concentrated, aqueous herbicidal compositions comprise about 0.5% w/v to about 5% w/v of an imidazolinyl acid salt, about 20% w/v to about 35% w/v of a glyphosate salt, about 0.5% w/v to about 4% w/v of dimethyl sulfoxide, about 1% w/v to about 15% w/v of a wetting agent, about 1% w/v to about 5% w/v of an antifreezing agent, up to about 0.5% w/v of an antifoaming agent, up to about 2.5% w/v of a base, and water, provided that the composition has an initial pH of from about 6.0 to about 6.8.

Advantageously, it has been found that the compositions of the present invention provide physically and chemically stable concentrated, aqueous herbicidal compositions of imidazolinyl acid salts and glyphosate salts. The stability of the compositions of this invention is achieved by including dimethyl sulfoxide in the compositions and limiting the initial pH of the compositions to a pH value of from about 6.0 to about 7.0. Beneficially, the compositions of this invention overcome the incompatibility problems associated with imidazolinyl acid salts and glyphosate salts without requiring the use of heavy aromatic solvents.

Imidazolinyl acid salts suitable for use in the stable compositions of this invention have the structural formula

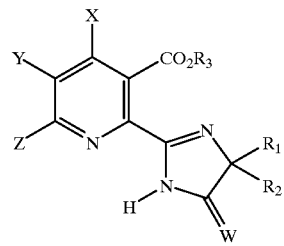

(I)

wherein
W is oxygen or sulfur;
$R_1$ is $C_1$–$C_4$alkyl;
$R_2$ is $C_1$–$C_4$alkyl or $C_3$–$C_6$cycloalkyl; and when $R_1$ and $R_2$ are taken together with the carbon to which they are attached they may represent $C_3$–$C_6$cycloalkyl optionally substituted with methyl;
X is hydrogen, halogen, hydroxyl or methyl;
Y and Z are independently hydrogen, halogen, $C_1$–$C_6$alkyl, $C_1$–$C_4$alkoxymethyl, hydroxyloweralkyl, $C_1$–$C_6$alkoxy, $C_1$–$C_4$alkylthio, phenoxy, $C_1$–$C_4$haloalkyl, nitro, cyano, $C_1$–$C_4$alkylamino, diloweralkylamino, or $C_1$–$C_4$alkylsulfonyl or phenyl optionally substituted with $C_1$–$C_4$-alkyl, $C_1$–$C_4$alkoxy or halogen, and when taken together, Y and Z may form a ring in which YZ are represented by the structure: —$(CH_2)_n$—, where n is an integer of 3 or 4, provided that X is hydrogen, or

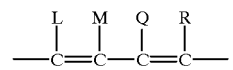

where L, M, Q and R are independently hydrogen, halogen, $C_1$–$C_4$alkyl or $C_1$–$C_4$alkoxy; and
$R_3$ is an ammonium, organic ammonium, trialkylsulfonium or alkali metal cation.

Preferred imidazolinyl acid salts for use in the compositions of this invention include 5-ethyl-2-(4-isopropyl-4-methyl-5-oxo-2-imidazolin-2-yl)nicotinic acid salts (imazethapyr acid salts);

2-(4-isopropyl-4-methyl-5-oxo-2-imidazolin-2-yl)-3-quinolinecarboxylic acid salts (imazaquin acid salts);

2-(4-isopropyl-4-methyl-5-oxo-2-imidazolin-2-yl) nicotinic acid salts (imazapyr acid salts);

2-(4-isopropyl-4-methyl-5-oxo-2-imidazolin-2-yl)-5-(methoxymethyl)nicotinic acid salts (imazamox acid salts); and 2-(4-isopropyl-4-methyl-5-oxo-2-imidazolin-2-yl)-5-methylnicotinic acid salts (imazapic acid salts); and mixtures thereof.

Glyphosate salts suitable for use in the compositions of the present invention include, but are not limited to, glyphosate salts wherein the cation portion of the salt is an ammonium, organic ammonium, trialkylsulfonium or alkali metal cation. Preferred glyphosate salts are glyphosate organic amine salts such as $C_1$–$C_6$alkylamine salts, di-($C_1$–$C_6$alkyl)-amine salts and tri-($C_1$–$C_6$alkyl)-amine salts with $C_1$–$C_6$alkylamine salts being more preferred. Glyphosate isopropylamine salt is especially suitable for use in the compositions of this invention.

In another preferred embodiment of the present invention, the cation portion of the imidazolinyl acid salt and the glyphosate salt are the same. In particular, it has been found that compositions comprising imazethapyr isopropylamine salt and glyphosate isopropylamine salt are physically and chemically stable.

In order to provide herbicidally effective amounts of the co-active ingredients, the ratio of the imidazolinyl acid salt to the glyphosate salt in the compositions of this invention is preferably about 1:4 to about 1:15, more preferably about 1:7 to about 1:12, on a weight to volume basis.

Wetting agents suitable for use in the compositions of this invention include, but are not limited to, conventional wetting agents such as ethoxylated tallow amines, alpha olefin sulfonate salts, alkylphenol polyethylene oxide condensates and the like and mixtures thereof. Preferred wetting agents include ethoxylated tallow amines having 15 moles of ethylene oxide per molecule (such as SURFOM 5204-CS available from Oxiteno, Maua, Sao Paulo, Brazil); sodium alpha olefin sulfonates (such as Witconate AOK available from Witco, Sao Paulo, Sao Paulo, Brazil); and nonylphenol ethoxylates (such as FLO MO®9N, available from Witco, New York, New York, United States); and mixtures thereof. Ethoxylated tallow amines are especially suitable for use in the stable compositions of this invention.

Antifreezing agents suitable for use in the compositions of the present invention include, but are not limited to, glycols such as propylene glycol and ethylene glycol, N-methylpyrrolidone, cyclohexanone, and alcohols such as ethanol and methanol. Preferred antifreezing agents include glycols with propylene glycol being an especially preferred antifreezing agent. Antifoaming agents suitable for use in this invention are conventional antifoaming agents including, but not limited to, silicone based antifoaming agents such as antifoam SE 47 (available from Wacker, Santo Amaro, Sao Paulo, Brazil).

In addition, the compositions of this invention may contain conventional additives used in aqueous compositions such as antimicrobial agents, antioxidants, buffers (including a $K_2HPO_4$/$KH_2PO_4$ mixture), dyes and the like and mixtures thereof.

A most preferred concentrated, aqueous herbicidal composition of this invention comprises about 2% w/v to about 4% w/v of imazethapyr isopropylamine salt, about 20% w/v to about 35% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 2.5% w/v of a base, and water, provided that the composition has an initial pH of from about 6.0 to about 6.8 and the ratio of the imazethapyr isopropylamine salt to the glyphosate isopropylamine salt is about 1:7 to about 1:12.

The present invention also relates to a process for the preparation of concentrated, aqueous herbicidal compositions. The process of this invention comprises:

(a) providing a first aqueous solution containing an imidazolinyl acid salt;

(b) dispersing into the first aqueous solution, dimethyl sulfoxide and optionally an antifreezing agent to produce a second aqueous solution;

(c) adding into the second aqueous solution, an aqueous solution of a glyphosate salt to produce a homogeneous solution while maintaining the pH above about pH 6.0 with a base;

(d) adjusting the pH of the homogeneous solution produced in step (c) to about pH 6.0 to about 7.0, if necessary;

(e) adding into the pH adjusted solution obtained in step (d), a wetting agent and optionally an antifoaming agent; and (f) adding water.

Bases suitable for maintaining the pH of the solution produced in step (c) above about pH 6.0 include, but are not limited to, ammonia and organic amines and the like and mixtures thereof. Preferred bases include organic amines such as isopropylamine.

In a preferred process of the present invention, the pH is adjusted in step (d) with an acid. Acids suitable for use in the process of this invention include mineral acids and organic acids with organic acids such as acetic acid being preferred.

The concentrated, aqueous herbicidal compositions of this invention are diluted with water and applied as dilute, aqueous sprays to the locus where weed control is desired. While the compositions of this invention are effective for controlling weeds when employed alone, they may also be used in combination with other biological chemicals, including other herbicides.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of concentrated, aqueous herbicidal compositions containing imazethapyr isopropylamine salt and glyphosate isopropylamine salt The concentrated, aqueous herbicidal compositions identified below in Table I are prepared according to the following generic procedure:

(1) prepare a first aqueous solution of imazethapyr isopropylamine salt from imazethapyr and isopropylamine;

(2) add dimethyl sulfoxide and optionally propylene glycol to the first aqueous solution to obtain a second aqueous solution;

(3) add an aqueous solution of glyphosate isopropylamine salt to the second aqueous solution to obtain a homogeneous solution while maintaining the pH above about pH 6.2 with a base;

(4) adjust the pH of the homogeneous solution to a pH value of about pH 6.2 to about pH 6.8 with a 10% w/w acetic acid solution;

(5) add SURFOM 5204-CS (ethoxylated tallow amine wetting agent) and antifoam SE 47 (antifoaming agent) to the pH-adjusted solution; and (6) add water.

TABLE I

Concentrated, Aqueous Herbicidal Compositions

Ingredient/% w/v

| Comp. No. | Imaz-ethapyr IPA salt | Glypho-sate IPA salt | DMSO | Propylene Glycol | Base[1] | SURFOM 5204-CS | Anti-foam SE 47 | Acetic Acid | $K_2HPO_4$ | $KH_2PO_4$ | Water | pH |
|---|---|---|---|---|---|---|---|---|---|---|---|---|
| 1 | 2.70 | 32.40 | 1.35 | 3.00 | a/0.81 | 15.66 | 0.01 | 0.16 | — | — | to 100 | 6.1 |
| 2 | 2.50 | 30.00 | 1.25 | 3.00 | a/0.75 | 14.50 | 0.01 | 0.15 | — | — | to 100 | 6.1 |
| 3 | 2.00 | 24.00 | 1.00 | 3.00 | a/0.80 | 11.80 | 0.01 | 0.12 | — | — | to 100 | 6.0 |
| 4 | 2.50 | 30.00 | 1.25 | 3.00 | a/0.75 | 14.50 | 0.01 | — | — | — | to 100 | 6.2 |
| 5 | 3.50 | 28.00 | 1.75 | 3.00 | a/1.06 | 13.53 | 0.01 | 0.21 | — | — | to 100 | 6.1 |
| 6 | 3.00 | 24.00 | 1.50 | 3.00 | a/0.90 | 11.80 | 0.01 | 0.18 | — | — | to 100 | 6.1 |
| 7 | 3.50 | 28.00 | 1.75 | 3.50 | a/1.06 | 13.53 | 0.01 | — | — | — | to 100 | 6.2 |
| 8 | 3.00 | 21.00 | 1.50 | 3.00 | b/1.50 | 10.15 | 0.01 | 0.12 | 0.05 | 0.02 | to 100 | 6.2 |
| 9 | 3.00 | 21.00 | 1.50 | 3.00 | a/0.78 | 10.15 | 0.01 | 0.07 | 0.05 | 0.02 | to 100 | 6.1 |
| 10 | 4.00 | 28.00 | 2.00 | 3.00 | b/2.00 | 13.63 | 0.01 | 0.01 | 0.02 | 0.07 | to 100 | 6.2 |
| 11 | 4.00 | 28.00 | 2.00 | 3.00 | a/1.04 | 13.53 | 0.01 | 0.01 | 0.02 | 0.07 | to 100 | 6.4 |
| 12 | 3.00 | 21.00 | 2.00 | 3.00 | a/0.90 | 10.15 | 0.01 | 0.18 | — | — | to 100 | 6.7 |
| 13 | 4.00 | 28.00 | 2.00 | 3.00 | a/1.20 | 13.53 | 0.01 | 0.24 | — | — | to 100 | 6.7 |
| 14 | 4.00 | 28.00 | 2.00 | 3.00 | a/1.20 | 13.53 | 0.01 | 0.24 | — | — | to 100 | 6.4 |
| 15 | 3.00 | 21.00 | 2.00 | 3.00 | a/0.90 | 10.15 | 0.01 | 0.18 | — | — | to 100 | 6.4 |
| 16 | 3.00 | 21.00 | 1.50 | 3.00 | a/0.90 | 10.15 | 0.01 | 0.18 | — | — | to 100 | 6.1 |
| 17 | 4.00 | 28.00 | 2.00 | 3.00 | a/1.90 | 13.53 | 0.01 | 0.24 | — | — | to 100 | 6.2 |
| 18 | 4.00 | 28.00 | 3.50 | 1.60 | a/1.20 | 13.53 | 0.01 | 0.24 | — | — | to 100 | 6.1 |
| 19 | 4.00 | 28.00 | 3.50 | — | a/1.20 | 13.53 | 0.01 | 0.24 | — | — | to 100 | 6.1 |
| 20 | 4.00 | 28.00 | 2.00 | 1.50 | a/1.20 | 13.53 | 0.01 | 0.24 | — | — | to 100 | 6.2 |
| 21 | 4.00 | 28.00 | 2.00 | 3.00 | a/1.20 | 13.53 | 0.01 | 0.24 | — | — | to 100 | 6.2 |
| 22 | 4.00 | 28.00 | 2.00 | — | a/1.20 | 13.53 | 0.01 | 0.24 | — | — | to 100 | 6.2 |
| 23 | 3.70 | 26.00 | 0.80 | — | b/1.92 | 12.55 | 0.01 | 0.18 | — | — | to 100 | 6.1 |
| 24 | 3.70 | 26.00 | 0.80 | — | b/1.92 | 12.55 | 0.01 | 0.18 | — | — | to 100 | 6.1 |
| 25 | 4.00 | 28.00 | 1.00 | — | b/2.06 | 13.53 | 0.01 | 0.24 | — | — | to 100 | 6.1 |

[1]a. isopropylamine
b. ammonia

EXAMPLE 2

Evaluation of the storage stability of concentrated, aqueous herbicidal compositions The storage stability of the concentrated, aqueous herbicidal compositions prepared in Example 1 are evaluated by storing samples of the compositions at room temperature (RT), 45° C. and 5° C. The samples are removed periodically and visually inspected for physical changes in the appearance of the compositions. The results are summarized in Table II. As can be seen from the data in Table II, the compositions of the present invention are especially stable for prolonged periods of time when stored above 5° C.

TABLE II

Storage Stability of Concentrated, Aqueous Herbicidal Compositions

Storage Period

| Comp. Number | Storage Temperature | 1 week | 2 weeks | 3 weeks | 1 month | 2 months | 3 months |
|---|---|---|---|---|---|---|---|
| 1 | RT | no change | no change | no change | no change | no change | no change |
|   | 45° C. | no change | no change | no change | no change | no change | no change |
|   | 5° C. | no change | no change | no change | no change | no change | no change |
| 2 | RT | no change | no change | no change | no change | no change | no change |
|   | 45° C. | no change | no change | no change | no change | no change | no change |
|   | 5° C. | no change | no change | no change | no change | no change | no change |
| 3 | RT | no change | no change | no change | no change | no change | no change |
|   | 45° C. | no change | no change | no change | no change | no change | no change |
|   | 5° C. | no change | no change | no change | no change | no change | no change |
| 4 | RT | — | — | — | — | — | no change |
|   | 45° C. | — | — | — | — | — | no change |
|   | 5° C. | — | — | — | — | — | crystal growth |
| 5 | RT | no change | no change | no change | no change | no change | no change |
|   | 45° C. | no change | no change | no change | no change | no change | no change |
|   | 5° C. | no change | no change | no change | no change | no change | no change |
| 6 | RT | — | — | — | — | — | no change |
|   | 45° C. | — | — | — | — | — | no change |
|   | 5° C. | — | — | — | — | — | crystal growth |

TABLE II-continued

Storage Stability of Concentrated, Aqueous Herbicidal Compositions

| Comp. Number | Storage Temperature | 1 week | 2 weeks | 3 weeks | 1 month | 2 months | 3 months |
|---|---|---|---|---|---|---|---|
| 7 | RT | no change | no change | no change | no change | no change | no change |
|  | 45° C. | no change | no change | no change | no change | no change | no change |
|  | 5° C. | no change | no change | no change | no change | no change | no change |
| 8 | RT | no change | no change | no change | no change | no change | no change |
|  | 45° C. | no change | no change | no change | no change | no change | no change |
|  | 5° C. | no change | no change | no change | no change | no change | no change |
| 9 | RT | no change | no change | no change | no change | no change | no change |
|  | 45° C. | no change | no change | no change | no change | no change | no change |
|  | 5° C. | no change | no change | no change | no change | no change | no change |
| 10 | RT | no change | no change | no change | no change | no change | no change |
|  | 45° C. | no change | no change | no change | no change | no change | no change |
|  | 5° C. | no change | no change | no change | no change | — | — |
| 11 | RT | no change | no change | no change | no change | no change | no change |
|  | 45° C. | no change | no change | no change | no change | no change | no change |
|  | 5° C. | no change | no change | no change | no change | — | — |
| 12 | RT | no change | no change | no change | no change | no change | no change |
|  | 45° C. | no change | no change | no change | no change | no change | no change |
|  | 5° C. | no change | no change | no change | no change | no change | no change |
| 13 | RT | no change | no change | no change | no change | no change | no change |
|  | 45° C. | no change | no change | separation | separation | separation | no change |
|  | 5° C. | no change | no change | no change | no change | no change | no change |
| 14 | RT | no change | no change | no change | no change | no change | no change |
|  | 45° C. | no change | no change | no change | no change | no change | no change |
|  | 5° C. | no change | no change | no change | no change | no change | no change |
| 15 | RT | no change | no change | no change | no change | no change | no change |
|  | 45° C. | no change | no change | no change | no change | no change | no change |
|  | 5° C. | no change | no change | no change | no change | no change | no change |
| 16 | RT | no change | no change | no change | no change | no change | no change |
|  | 45° C. | no change | no change | no change | no change | no change | no change |
|  | 5° C. | no change | no change | no change | no change | no change | no change |
| 17 | RT | no change | no change | no change | no change | no change | no change |
|  | 45° C. | no change | no change | no change | no change | no change | no change |
|  | 5° C. | no change | no change | no change | no change | no change | no change |
| 18 | RT | no change | no change | no change | no change | no change | no change |
|  | 45° C. | no change | no change | no change | no change | no change | no change |
|  | 5° C. | no change | no change | crystal growth | crystal growth | crystal growth | crystal growth |
| 19 | RT | no change | no change | no change | no change | no change | no change |
|  | 45° C. | no change | no change | no change | no change | no change | no change |
|  | 5° C. | no change | crystal growth | crystal growth | crystal growth | crystal growth | crystal growth |
| 20 | RT | no change | no change | no change | trace crystal growth | trace crystal growth | trace crystal growth |
|  | 45° C. | no change | no change | no change | no change | — | no change |
|  | 5° C. | no change | crystal growth | crystal growth | crystal growth | crystal growth | crystal growth |
| 21 | RT | no change | no change | no change | trace crystal growth | trace crystal growth | trace crystal growth |
|  | 45° C. | no change | no change | no change | no change | no change | no change |
|  | 5° C. | no change | crystal growth | crystal growth | crystal growth | crystal growth | crystal growth |
| 22 | RT | no change | no change | no change | trace crystal growth | trace crystal growth | trace crystal growth |
|  | 45° C. | no change | no change | no change | no change | no change | no change |
|  | 5° C. | no change | crystal growth | crystal growth | crystal growth | crystal growth | crystal growth |
| 23 | RT | no change | no change | no change | trace crystal growth | crystal growth | trace crystal growth |
|  | 45° C. | no change | no change | no change | no change | no change | no change |
|  | 5° C. | crystal growth | crystal growth | crystal growth | crystal growth | — | — |
| 24 | RT | no change | no change | no change | trace crystal growth | crystal growth | trace crystal growth |
|  | 45° C. | no change | no change | no change | no change | no change | no change |
|  | 5° C. | no change | crystal growth | crystal growth | crystal growth | — | — |
| 25 | RT | no change | crystal growth | crystal growth | crystal growth | crystal growth | crystal growth |
|  | 45° C. | no change | no change | no change | no change | no change | no change |
|  | 5° C. | crystal growth | crystal growth | crystal growth | — | — | — |

EXAMPLE 3

Comparative evaluations of the storage stability of concentrated, aqueous herbicidal compositions The storage stability of composition numbers 20, 21 and 22 from Example 1 are compared to comparative compositions A, B and C. Comparative compositions A, B and C are essentially identical to compositions 20, 21 and 22, respectively, except that compositions A, B and C each have an initial pH value of 5.8. The compositions are evaluated according to the procedure described in Example 2, and the results are summarized in Table III.

As can be seen from the data in Table III, the compositions of the present invention, which have an initial pH value of 6.2, are more storage stable than the comparative compositions which have an initial pH value of 5.8.

imazapyr acid salt, an imazamox acid salt and an imazapic acid salt and mixtures thereof.

TABLE III

Comparative Storage Stability Evaluations

| Composition Number | Initial pH | Storage Temperature | 1 week | Storage Period 2 weeks | 3 weeks | 1 month |
|---|---|---|---|---|---|---|
| 20 | 6.2 | RT | no change | no change | no change | trcae crystal growth |
|  | 6.2 | 45° C. | no change | no change | no change | no change |
|  | 6.2 | 5° C. | no change | crystal growth | crystal growth | crystal growth |
| A | 5.8 | RT | crystal growth | crystal growth | crystal growth | crystal growth |
|  | 5.8 | 45° C. | no change | no change | no change | no change |
|  | 5.8 | 5° C. | crystal growth | crystal growth | crystal growth | crystal growth |
| 21 | 6.2 | RT | no change | no change | no change | trace crystal growth |
|  | 6.2 | 45° C. | no change | no change | no change | no change |
|  | 6.2 | 5° C. | no change | crystal growth | crystal growth | crystal growth |
| B | 5.8 | RT | crystal growth | crystal growth | crystal growth | crystal growth |
|  | 5.8 | 45° C. | no change | no change | no change | no change |
|  | 5.8 | 5° C. | crystal growth | crystal growth | crystal growth | crystal growth |
| 22 | 6.2 | RT | no change | no change | no change | trcae crystal growth |
|  | 6.2 | 45° C. | no change | no change | no change | no change |
|  | 6.2 | 5° C. | no change | crystal growth | crystal growth | crystal growth |
| C | 5.8 | RT | crystal growth | crystal growth | crystal growth | crystal growth |
|  | 5.8 | 45° C. | no change | no change | no change | no change |
|  | 5.8 | 5° C. | crystal growth | crystal growth | crystal growth | crystal growth |

What is claimed is:

1. A concentrated, aqueous herbicidal composition which comprises about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 3% w/v of a base, and water, provided that the composition has an initial pH of from about 6.0 to about 7.0.

2. The composition according to claim 1 which comprises about 0.5% w/v to about 5% w/v of the imidazolinyl acid salt, about 20% w/v to about 35% w/v of the glyphosate salt, about 0.5 w/v to about 4% w/v of dimethyl sulfoxide, about 1% w/v to about 15% w/v of the wetting agent, about 1% w/v to about 5% w/v of the antifreezing agent, up to about 0.5% w/v of the antifoaming agent, up to about 2.5% w/v of the base, and water, provided that the composition has an initial pH of from about 6.0 to about 6.8.

3. The composition according to claim 1 wherein the ratio of the imidazolinyl acid salt to the glyphosate salt is about 1:4 to about 1:15.

4. The composition according to claim 3 wherein the ratio is about 1:7 to about 1:12.

5. The composition according to claim 1 wherein the initial pH is from about 6.0 to about 6.8.

6. The composition according to claim 1 wherein the cation portion of the imidazolinyl acid salt and the glyphosate salt is the same.

7. The composition according to claim 6 wherein the cation portion of the imidazolinyl acid salt and the glyphosate salt is an ammonium, organic ammonium, trialkylsulfonium or alkali metal cation.

8. The composition according to claim 7 wherein the cation is an organic ammonium cation.

9. The composition according to claim 8 wherein the organic ammonium cation is isopropylammonium.

10. The composition according to claim 1 wherein the imidazolinyl acid salt is selected from the group consisting of an imazethapyr acid salt, an imazaquin acid salt, an 11. The composition according to claim 10 wherein the imidazolinyl acid salt is an imazethapyr acid salt.

12. The composition according to claim 1 wherein the wetting agent is selected from the group consisting of an ethoxylated tallow amine, an alpha olefin sulfonate salt and an alkylphenol polyethylene oxide condensate and mixtures thereof, the antifreezing agent is a glycol, and the base is selected from the group consisting of ammonia and an organic amine and mixtures thereof.

13. The composition according to claim 12 wherein the wetting agent is an ethoxylated tallow amine, the glycol is propylene glycol, and the base is isopropylamine.

14. The composition according to claim 1 which comprises about 2% w/v to about 4% w/v of imazethapyr isopropylamine salt, about 20% w/v to about 35% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 2.5% w/v of a base, and water, provided that the composition has an initial pH of from about 6.0 to about 6.8 and the ratio of the imazethapyr isopropylamine salt to the glyphosate isopropylamine salt is about 1:7 to about 1:12.

15. A process for the preparation of a concentrated, aqueous herbicidal composition which process comprises:
(a) providing a first aqueous solution containing an imidazolinyl acid salt;
(b) dispersing into the first aqueous solution, dimethyl sulfoxide and optionally an antifreezing agent to produce a second aqueous solution;
(c) adding into the second aqueous solution, an aqueous solution of a glyphosate salt to produce a homogeneous solution while maintaining the pH above about pH 6.0 with a base;
(d) adjusting the pH of the homogeneous solution produced in step (c) to about pH 6.0 to about pH 7.0, if necessary;
(e) adding into the pH adjusted solution obtained in step (d), a wetting agent and optionally an antifoaming agent; and (f) adding water.

16. The process according to claim 15 wherein the pH is adjusted in step (d) with an acid.

17. The process according to claim 15 wherein the concentrated, aqueous herbicidal composition comprises about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, about 0.5% w/v to about 3% w/v of a base, and water, provided that the composition has an initial pH of from about 6.0 to about 7.0.

18. The process according to claim 15 wherein the cation portion of the imidazolinyl acid salt and the glyphosate salt is the same.

19. The process according to claim 18 wherein the cation portion of the imidazolinyl acid salt and the glyphosate salt is an ammonium, organic ammonium, trialkylsulfonium or alkali metal cation.

20. The process according to claim 19 wherein the cation is isopropylammonium.

21. The process according to claim 15 wherein the ratio of the imidazolinyl acid salt to the glyphosate salt is about 1:4 to about 1:15.

22. The process according to claim 15 wherein the imidazolinyl acid salt is imazethapyr isopropylamine salt and the glyphosate salt is glyphosate isopropylamine salt.

23. A concentrated, aqueous herbicidal composition comprising about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, about 0.5% w/v to about 3% w/v of a base, and water, provided that the composition has an initial pH of from about 6.0 to about 7.0, which composition is prepared by the process of claim 15.

* * * * *